United States Patent [19]

Simpson et al.

[11] Patent Number: 5,004,684
[45] Date of Patent: Apr. 2, 1991

[54] METHOD FOR ATP EXTRACTION

[75] Inventors: William J. Simpson, Salfords; John R. M. Hammond, Oxted, both of England

[73] Assignee: Lumac BV, Landgraaf, Netherlands

[21] Appl. No.: 246,455

[22] Filed: Sep. 19, 1988

[30] Foreign Application Priority Data

Sep. 22, 1987 [GB] United Kingdom ................ 8722252

[51] Int. Cl.$^5$ ........................... C12Q 1/66; C12N 1/06
[52] U.S. Cl. ....................................... 435/8; 435/259; 435/39; 435/810; 436/17
[58] Field of Search ...................... 436/17, 18; 435/34, 435/7, 8, 39, 259, 810

[56] References Cited

U.S. PATENT DOCUMENTS 4,102,810  7/1978  Armstrong ........................... 252/408

OTHER PUBLICATIONS

Thore et al., J. Clin. Microbiol., 1(1), 1-8, 1975 Detection of Bacteriuria by Luciferase Assay of ATP.
Richards et al., Chem. Abstracts 84: 100095n, 1976 Electron Microscope Study of Effect of Benzalkonium Chloride and Edetate Disodium on Cell Envelope of *Pseudomonas aeruginosa*.

*Primary Examiner*—Esther L. Kepplinger
*Assistant Examiner*—Laurie A. Scheiner
*Attorney, Agent, or Firm*—Frishauf, Holtz, Goodman & Woodward

[57] ABSTRACT

A method for the extraction of ATP from a microorganism which comprises contacting said microroganism with an ATP releasing agent and thereafter contacting the resultant solution with a neutralizing agent which acts substantially to eliminate the distorting effect of the releasing agent on subsequent ATP assay.

5 Claims, 2 Drawing Sheets

METHOD FOR ATP EXTRACTION

TECHNICAL FIELD OF THE INVENTION

The present invention relates to a method for the extraction of ATP from a microorganism, and particularly to a method for such an extraction which reduces subsequent distortions on assay with firefly luciferase.

Detection of brewery microorganisms, for quality and process control purposes, is presently carried out using solid or liquid culture media and incubation periods of three to seven days are required before the results of tests are known. The historical nature of brewery microbiological results presents a problem in that, due to the high cost of warehouse space, beer sometimes has to be despatched to the retail outlet before the results of tests are known. Alternatively, the beer must be stored in the brewery warehouse. Many brewers do not have sufficient warehouse space at their disposal to implement this option. Often therefore, if the results of microbiological analyses require that corrective action be taken, the beer must be returned from the retail outlet to the brewery.

Many other industries have a requirement for rapid microbial monitoring techniques. Probably most important of all is the food industry's need to monitor food destined for human consumption for the presence of pathogenic organisms (most notably food poisoning organisms). In addition, rapid detection techniques for microorganism are required in such diverse areas as clinical chemistry, the water industry, the textile industry and the pharmaceutical industry, where product spoilage, public health, or legislation produces a need for such methodologies.

The use of rapid microbial monitoring techniques in the brewing industry offers several advantages over conventional methods:
1. reduction in process risk and uncertainty
2. elimination or reduction in the level of trade returns
3. corrective action can be taken in response to the results, reducing costly beer reprocessing. Advantages of a similar nature apply in other industries.

PRIOR ART

One of the most promising methods available for rapid microbial monitoring is one based on the measurement of microbial adenosine triphosphate (ATP) with the firefly luciferase reaction. ATP is found in live cells but not in dead cells. In the presence of purified enzyme (luciferase) and substrate (D-luciferin) from the American firefly (*Photinus pyralis*) and sufficient magnesium as cofactor, the following reaction takes place:

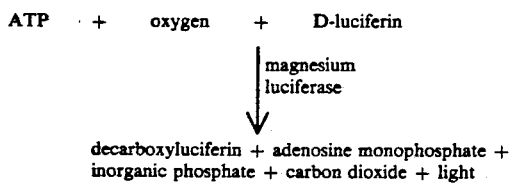

The amount of light produced by the reaction is directly proportional to the ATP concentration and is detected using a sensitive light detector. ATP concentrations of as low as $1 \times 10^{-18}$ M can be detected using this assay system. To estimate the concentration of microbial ATP in a sample, the ATP must first be extracted from the microorganism. Maximum assay sensitivity can only be achieved when:
i) light output is not reduced (quenched) by the extract or extractant
ii) cell extracts are not diluted before carrying out the assay The cationic surface agents, benzalkonium chloride (see Siro et al., *European Journal of Applied Microbiology and Biotechnology* 1982, 15, 258–264) and dodecyl trimethyl ammonium bromide (see Lundin pp. 491–501 in: *Analytical Applications of Bioluminescence and Chemiluminescence*. Kricka, L.J. et al. (Eds) Academic Press, London, 1984) have been used to extract microbial ATP from yeast, and yeast and bacteria, respectively. Although Lundin and Siro et al. could extract ATP from microorganisms with these cationic detergents, they found that the extracts resulting from such procedures adversely affected the luciferase reaction, bringing about a rapid decay in light output. As a result, considerable dilution of the extract was required before the ATP assay could be performed on such samples, hence lowering the sensitivity of the assay. As an alternative procedure to dilution, Lundin found that, in the case of dodecyl trimethylammonium bromide, the decay of light output could be reduced by addition of protein (bovine serum albumin) to the assay. However, the concentration of albumin required (2.5–10% w/v) inhibited light output strongly, again reducing the sensitivity of the assay.

The use of surface active agents to extract microbial ATP is discussed in GB-A-1604249: Kolehmainen, S. and Tarkkanen, V.: Selective Measurement of Somatic and Microbial Cells. In this disclosure is suggested the use of both ethoxylated amines and quarternary ethoxylated amines for the extraction of ATP. By careful manipulation of the ratio of one surface active agent to the other they could limit (but not eliminate) the decay in reaction rate associated with such compounds. However, these extractants still effected an increase in light output from the reaction, thus reducing assay precision.

One commercially available ATP releasing agent (Nucleotide Releasing Buffer (NRB); Lumac BV, the Netherlands) is claimed by the manufacturer to be a mixture of "ionic detergents", however (in a similar fashion to those compounds described above) unless diluted before performing the ATP assay, extracts made with this reagent also effect the kinetics of the luciferase reaction.

Other available extraction methods (see Stanley, P.E. in: *Methods in Enzymology*, 1986, 133, 14–22) such as trichloroacetic acid extraction and dimethylsulphoxide extraction, although extracting ATP efficiently from microorganism, again require dilution before carrying out the ATP assay because the extractant interferes with the luciferase reaction.

The non-ionic detergent polyoxyethylene sorbitan monooleate (Tween 80) is used in microbiological applications for the inactivation of many antimicrobial compounds, including quaternary ammonium compounds (see Russel et al., *Journal of Applied Bacteriology*, 1979, 46, 207–245). For instance, during tests to determine the efficacy of antimicrobial agents, the compound is used to inactivate any of the antimicrobial agent which may have been carried over with the inoculum. If any antimicrobial agent remained in the system, it could continue to act, resulting in an overestimation of the efficacy of the antimicrobial activity of the substance. The principle has not hitherto been applied to the inactivation of an ATP extractant for the purpose of ensuring biochemical compatibility with the assay system. In fact, non-ionic detergents have been shown to affect the kinetics of the firefly luciferase reaction, increasing reaction rate, under some conditions (see Kricka, L. J. & DeLuca, M., Archives of Biochemistry and Biophysics, 1982, 217, 674–681)

SUMMARY OF THE INVENTION

According to the present invention there is provided a method for the extraction of ATP from a microorganism which comprises contacting said microorganism with an ATP releasing agent and contacting the resultant solution is with a neutralising agent which acts substantially to eliminate the distorting effect of the releasing agent on subsequent ATP assay. The releasing agent is perferably a cationic surface active agent which is perferably contacted with a non-ionic surface active neutralising agent. The neutralising agent is preferably used a greater concentration than the releasing agent in order to neutralise all residues of the releasing agent. The nonionic surface active agent is preferably selected from Tween 20, Tween 60, Tween 80, Polyoxyethylene ether W1, or Triton X-100.

The Tween surfactants are tradenames for polyethylene sorbitol esters. Tween 30 is polyethylene glycol (20) sorbitan monolaurate; Tween 60 is polyethylene glycol (20) sorbitan monostearate; and Tween 80 is polyethylene glycol (20) sorbitan monooleate. Triton X-100 is a tradename for polyethylene glycol (9,10 ) p-t-octylphenyl.

The assay may be performed by:
a) pipetting an aliquot of 10–200ul of a sample into a transparent cuvette;
b) pipetting 10–200 ul of the releasing agent into the cuvette to extract ATP;
c) pipetting into the cuvette 10–200ul of the neutralising agent into a concentration higher than the releasing agent in order to neutralise the releasing agent;
d) placing the cuvette into a luminescent photometer;
e) measuring the amount of bioluminescent light produced by ATP in the cuvette after an addition of 50–200 ul of a firefly luciferin-luciferase reagent in a biochemical buffer having a pH of 7.2–8.5;
f) adding a known amount of ATP in 10–20ul into the measured cuvette and measuring the amount of bioluminescent in the cuvette again; and
g) calculating the amount of ATP in the sample by these two bioluminescent light readings using the internal standardization principle.

According to the present invention there is also provided a kit for the assay of ATP in the microorganism sample, the kit comprising:
a) an assay buffer ;
b) a firefly—luciferin preparation;
c) a cationic surface active agent; and
d) a non-ionic surface active agent.
Preferably, the assay buffer has a pH of 7.2–8.2, more preferably about 7.75. Preferably, the assay buffer includes an agent for chelation of divalent cations.

DETAILED DESCRIPTION

The present invention thus provides a simple procedure for the extraction of ATP from microorganisms in such a way that the extracts so produced do not affect the kinetics of the firefly luciferase reaction used for the assay of the extracted ATP, thus facilitating maximum assay sensitivity and precision. The procedure involves extracting the ATP from a suspension of the microorganism with a cationic surface active agent (detergent), then neutralising the cationic surface active agent. In this way, interference with the luciferase reaction by the cationic detergent (see Example 1) is avoided. All reagents are buffered to a range of pH 7.2–8.2, although pH 7.75, the optimum pH for the firefly reaction is preferred. The buffer may contain an agent to chelate divalent cations which may be ethylene diamine tetraacetic acid (EDTA), thus inhibiting the action of ATP degrading enzymes which may be present in cell extracts. The extracts produced using this technique are highly compatible with firefly luciferase and are thus ideally suited for use in systems employing the enzyme in an immobilised form. the low level detection of microorganism, dilution of the extracts must be avoided and for this reason the present invention represents a significant advance over available procedures.

The procedures outlined in the present invention do not result in any interference in the luciferase ATP-assay in terms of either sensitivity or precision. Sensitivity is optimal because:
(a) the extractant does not significantly affect the intensity of light emission from the luciferase system,
(b) the extractant is highly soluble in aqueous systems and can therefore be applied to the cell menstrum in a concentrated form.

Precision is optimal because the extractant does not affect the kinetics of the assay system; calculation of an unknown concentration of ATP from comparison with the response obtained from a known concentration of ATP (the internal standard technique) is not subject to errors brought about by changes in the reaction rate.

Figure 1:
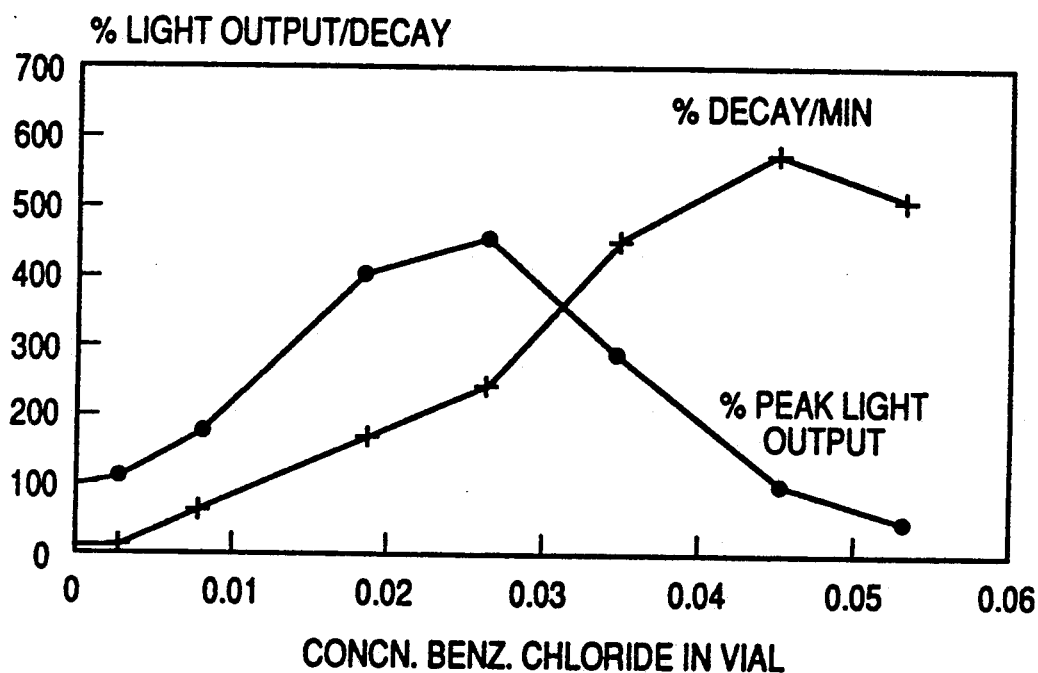
Figure 2:
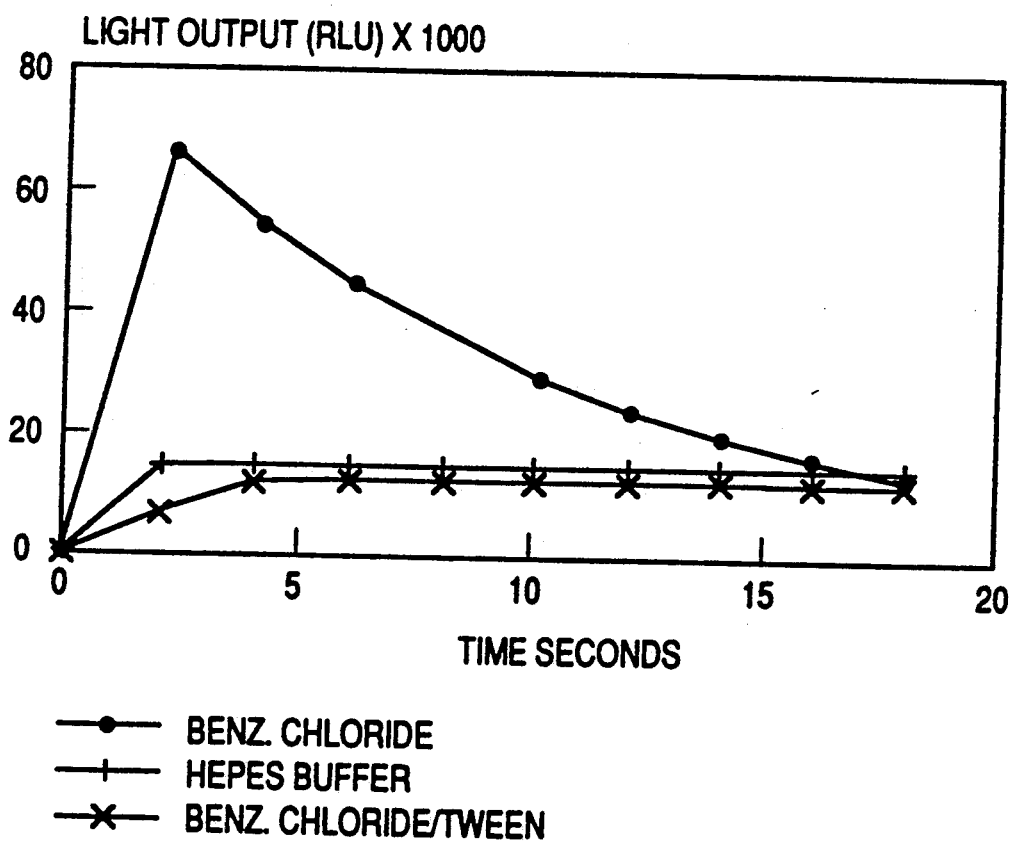

The invention will now be illustrated in the following Examples and with reference to the accompanying drawings wherein:

FIG. 1 shows the effect of the releasing agent Benzethonium chloride on the kinetics of LUMIT PM and FIG. 2 shows the effects of the releasing agent Benzethonium chloride on the kinetics of LUMIT PM, with or without a non-ionic detergent.

EXAMPLE 1

Effect of the quaternary ammonium compound benzethonium chloride on a commercial firefly luciferase/luciferin reagent One picomole of ATP standard (1pM in 10$\mu$l) was transferred to a cuvette. To this was added 100 ul of:
(a) assay buffer (N-2-Hydroxyethylpiperazine-N-2-ethanesulfonic acid(HEPES) 0.025M: 2mM Ethylenediamine tetraacetic acid (EDTA), pH 7.75), or
(b) benzethonium chloride (0.008–0.16% w/v in assay buffer pH 7.75).

The luminescent reaction was started by the addition of 100 ul of a commercial firefly luciferase/luciferin preparation (Lumit PM, Lumac BV, the Netherlands). Light output was monitored continuously to check signal stability using a LUMAC 2010A biocounter connected to an LKB plotter. The results are shown in FIG. 1. Benzethonium chloride bring about a decay of reaction rate (light output) at all concentrations and an increase in light output at some concentrations.

EXAMPLE 2

Kinetics of a commercial firefly luciferase/luciferin reagent in the presence of benzethonium chloride with or without the neutralising agent Tween 80

One picomole of APT standard (1pM in 10ul) was transferred to a cuvette. To this was added one of the following:
(a) 200μl of assay buffer (see Example 1)
(b) 200μl 0.02% benzethonium chloride in assay buffer
(c) 100μl 0.04% benzethonium chloride in assay buffer, then 100ul 2.2% Tween 80 in assay buffer. All reactions were started by the addition of 100ul Lumit PM. Light output was monitored continuously as in Example 1. The results are shown in FIG. 2. The increase in light output and increased decay rate induced by benzethonium chloride is prevented in the presence of Tween 80.

EXAMPLE 3

Comparison of methods for extraction of ATP from microorganisms

Comparison of extraction methods i) Preparation of test organisms

*Saccharomyces cerevisiae* NCYC 1342, *Lactobacillus brevis* BSO 28 and *Obesumbacterium proteus* BSO 434 were grown in 10ul volumes of liquid media at 25° C. without shaking: *Sacc. cerevisiae* and *O. proteus* were grown on WLM medium (Oxoid Ltd., Basingstoke, Hants, Product No. CM 309), *L. brevis* was grown in MRS medium (Oxoid Ltd, Product No. CM 359) (BSO: Beer spoilage organism collection, Brewing Research Foundation, Nutfield, Redhill, Surrey RH1 4HY, U.K.; NCYC: National Collection of Yeast Cultures, Norwich NR4 7UA, U.K.). Organisms were diluted in sterile deionised water to the desired concentration prior to extraction.

ii) Extraction of ATP from test organisms

ATP was extracted from dilutions of each test organism with one of the following:
a) equal volumes of Nucleotide Releasing Buffer (NRB, Lumac BV, The Netherlands) and sample
b) equal volumes of 0.08% (w/v) benzethonium chloride and sample
c) nine volumes of dimethylsulphoxide (DMSO) to one volume of sample
d) equal volumes of trichloroacetic acid (TCA) (10%, 5%, 2.5% or 1.25% w/v) and sample.

Mixing of sample and extractant was assisted by the pipetting action used and agitation of the cuvettes. All extraction procedures were performed at room temperature.

iii) Preparation of extracts for assay a) NRB extracts were diluted 1:10 with assay buffer pH 7.75
b) BAX (Brewing Research Foundation ATP Extractant): benzethonium chloride; equal volumes of the
b) BAX (Brewing Research Foundation ATP Extractant): benzethonium chloride; equal volumes of the extract and 2.2% Tween 80 (in assay buffer pH 7.75) were mixed. The resulting mixture was diluted 1:10 with assay buffer pH 7.75.
c) DMSO: extracts were diluted 1:50 with assay buffer pH 7.75
d) TCA: extracts were diluted 1:50 with assay buffer pH 7.75 iv) ATP assay of extracts

One hundred microliters of each extract were transferred to a cuvette and 100μl Lumit PM were then added. The cuvette was placed immediately in the Biocounter and the light output integrated over a 10 second interval. Ten microliters of ATP standard (1pM) were then added to the cuvette and the light output integrated over a further 10 second period.

v) Calculation of ATP concentration

ATP concentrations in the extracts were calculated with respect to the light response obtained from the ATP standard. Dilution of the NRB extract removed the need to correct the results for distortion associated with light decay.

The results are shown in Table 1. The procedure which is the subject of this patent application extracted ATP efficiently from all the organisms tested. (n.b. The dilution step applied to the extracts produced in this Example served to lower the ATP levels in the extracts to a level compatible with the ATP assay system. For the extraction procedure which is the subject of this patent application no dilution is necessary when only low levels of ATP are present in the sample. However, a dilution step is needed with the other methods if quenching and signal decay are to be avoided).

The invention provides therefore a method for the extraction of ATP as hereinbefore set forth, and to assay kits for performing such methods.

TABLE 1

Comparison of ATP extraction methods

| extraction method+ | $[ATP] \times 10^{-18}$ M/cell | | |
|---|---|---|---|
| | Sacc. cerevisiae NCYC 1342 | L. brevis BSO 28 | O. proteus BSO 434 |
| BAX | 353 (112)* | 5.74 (78) | 1.85 (95) |
| NRB | 370 (117) | 2.42 (37) | 1.73 (89) |
| DMSO | 372 (118) | 7.25 (110) | 2.47 (126) |
| TCA (1.25%) | 32 (10) | 6.59 (100) | 1.95 (100) |
| TCA (2.5%) | 61 (19) | 6.42 (97) | 1.81 (93) |
| TCA (5.0%) | 314 (99) | 6.16 (94) | 1.71 (90) |
| TCA (10.0%) | 316 (100) | 6.10 (93) | 1.69 (86) |

*figures in parenthesis represent the % extraction efficiency with respect to the most efficient concentration of TCA employed.
+cell concentrations extracted were: *Sacc. cerevisiae* $4.0 \times 10^5$ ml$^{-1}$, *L. brevis* $3.8 \times 10^7$ ml$^{-1}$, *O. proteus* $8.1 \times 10^7$ ml$^{-1}$.

What is claimed is:

1. In a method for the assay of ATP from a microorganism which comprises contacting a sample containing said microorganism with an ATP releasing agent consisting essentially of an effective amount to release ATP of a cationic surface active agent, and thereafter determining the ATP released into the sample using a luciferin-luciferase reagent, the improvement which comprises eliminating the distorting effect of the releasing agent on the ATP assay, by addition of an amount of a non-ionic surface active agent to be effective as a neutralizing agent for the releasing agent after addition of said releasing agent and before said ATP assay.

2. A method in accordance with claim 1 wherein the releasing agent is benzethonium chloride in a concentration of 0.008–0.16% w/v.

3. A method in accordance with claim 1 wherein the non-ionic surface active agent is used in a greater concentration than the releasing agent in order to neutralize all residues of the releasing agent.

4. A method in accordance with claim 1 wherein the non-ionic surface active agent is selected from the group consisting of polyethylene glycol (20) sorbitan monolaurate; polyethylene glycol (20) sorbitan monostearate; polyethylene glycol (20) sorbitan monooleate; and polyethylene glycol (9,10) p-t-octylphenol.

5. A method in accordance with claim 1 wherein the assay is performed by:
   a) pipetting an aliquot of 10–200µl of a sample into a transparent cuvette;
   b) pipetting 10–200µl of the cationic surface active agent into said cuvette to extract ATP;
   c) pipetting into said cuvette 10–200µl of the non-ionic surface active agent in a concentration higher than the cationic surface active agent in order to neutralize the releasing agent;
   d) placing the cuvette in a luminescent photometer;
   e) measuring the amount of bioluminescent light produced by ATP in the cuvette after an addition of 50–200µl of a firefly luciferin-luciferase reagent in a biochemical buffer having a pH of 7.2–8.2;
   f) adding a known amount of ATP in 10–20µl into the measured cuvette and measuring the amount of bioluminescence in the cuvette again; and
   g) calculating the amount of ATP in the sample from these two bioluminescent light readings using the internal standardization principle.

* * * * *